United States Patent
Tunnicliffee et al.

(10) Patent No.: US 10,162,031 B2
(45) Date of Patent: Dec. 25, 2018

(54) METHOD AND SYSTEM FOR DETERMINING A CORRECTED VALUE OF MAGNETIC RESONANCE RELAXOMETRY DATA OF A SUBJECT'S VISCERAL TISSUE FOR EXTRACELLULAR FLUID BASED ON A NORMAL IRON CONTENT FOR THE VISCERAL TISSUE

(71) Applicant: Isis Innovation Limited, Oxford (GB)

(72) Inventors: Elizabeth Tunnicliffee, Oxford (GB);
Matthew Robson, Oxford (GB);
Rajarshi Banerjee, Oxford (GB)

(73) Assignee: ISIS INNOVATION LIMITED, Oxford (GB)

( * ) Notice: Subject to any disclaimer, the term of this patent is extended or adjusted under 35 U.S.C. 154(b) by 474 days.

(21) Appl. No.: 14/775,864

(22) PCT Filed: Mar. 14, 2014

(86) PCT No.: PCT/GB2014/050815
§ 371 (c)(1),
(2) Date: Sep. 14, 2015

(87) PCT Pub. No.: WO2014/140635
PCT Pub. Date: Sep. 18, 2014

(65) Prior Publication Data
US 2016/0025831 A1    Jan. 28, 2016

(30) Foreign Application Priority Data
Mar. 15, 2013   (GB) .................................. 1304728.7

(51) Int. Cl.
*G01R 33/50*   (2006.01)
*A61B 5/00*    (2006.01)
(Continued)

(52) U.S. Cl.
CPC ............ *G01R 33/50* (2013.01); *A61B 5/0044* (2013.01); *A61B 5/055* (2013.01);
(Continued)

(58) Field of Classification Search
CPC .... G01R 33/50; G01R 33/448; A61B 5/0044; A61B 5/14546; A61B 5/055; G06T 7/0012; G06T 2207/30056; G06T 2207/10088
See application file for complete search history.

(56) References Cited

U.S. PATENT DOCUMENTS

| 5,218,532 A | 6/1993 | Mori |
| 5,322,682 A | 6/1994 | Bartzokis |

(Continued)

FOREIGN PATENT DOCUMENTS

| DE | 102009011382 | 9/2010 |
| GB | 2498254 | 9/2010 |

(Continued)

OTHER PUBLICATIONS

Vymazal et al., 1992 T1 and T2 of ferritin at different field strengths: Effect on MRI. Magn Reson Med. 1992; 27:367-74.

(Continued)

*Primary Examiner* — G. M. Hyder
(74) *Attorney, Agent, or Firm* — Thomas|Horstemeyer, LLP (57) ABSTRACT

The present disclosure provides systems and methods which may assist in evaluating liver fibrosis/inflammation in the presence of elevated iron using magnetic resonance relaxometry. In a non-limiting embodiment, the systems and methods include: obtaining a measurement of relaxometry data of a subject's liver for extracellular fluid, preferably using a magnetic resonance imaging (MRI) device; determining an iron content for the liver; simulating a measure- (Continued)

ment of the subject's liver for extracellular fluid for the determined iron content; comparing the measurement of the subject's liver for extracellular fluid to the simulated measurement of the subject's liver for extracellular fluid; and determining from said comparison a value of extracellular fluid in the subject's liver based on a normal iron content for the liver. The simulation can include multi-compartment modeling of various fractions of extracellular fluid in the liver and the impact of iron content in the liver on both the intra- and extracellular relaxation times.

24 Claims, 4 Drawing Sheets (51) Int. Cl.
    *A61B 5/055*       (2006.01)
    *A61B 5/145*       (2006.01)
    *G01R 33/44*       (2006.01)
    *G06T 7/00*         (2017.01)

(52) U.S. Cl.
    CPC ........ *A61B 5/14546* (2013.01); *G01R 33/448* (2013.01); *G06T 7/0012* (2013.01); *G06T 2207/10088* (2013.01); *G06T 2207/30048* (2013.01); *G06T 2207/30056* (2013.01)

(56) References Cited

U.S. PATENT DOCUMENTS

| | | | |
|---|---|---|---|
| 5,908,386 | A | 6/1999 | Ugurbil et al. |
| 5,993,398 | A | 11/1999 | Alperin |
| 6,245,027 | B1 | 6/2001 | Alperin |
| 6,605,943 | B1 | 8/2003 | Clark et al. |
| 2004/0102692 | A1 | 5/2004 | Schenck |
| 2004/0155653 | A1 | 8/2004 | Larson et al. |
| 2005/0197586 | A1 | 9/2005 | Pearlman |
| 2007/0247153 | A1 | 10/2007 | Yu et al. |
| 2008/0012563 | A1 | 1/2008 | Weiss |
| 2008/0150532 | A1 | 6/2008 | Slavin et al. |
| 2010/0198050 | A1 | 8/2010 | Mori |
| 2010/0241012 | A1 | 9/2010 | Yin et al. |
| 2011/0028828 | A1 | 2/2011 | Daye et al. |
| 2011/0181285 | A1 | 7/2011 | Greiser |
| 2013/0248533 | A1 | 9/2013 | Wallis et al. |
| 2014/0330106 | A1* | 11/2014 | Banerjee ............ G01R 33/4828 600/410 |

FOREIGN PATENT DOCUMENTS

| | | |
|---|---|---|
| GB | 2513474 | 10/2014 |
| GB | 2524587 | 9/2015 |
| WO | WO 2006134430 | 12/2006 |
| WO | WO 2008/144391 | 11/2008 |
| WO | 20130046158 | 4/2013 |
| WO | WO 2013/046158 | 4/2013 |
| WO | 20130088149 | 6/2013 |
| WO | 20130088151 | 6/2013 |
| WO | WO 2013/088149 | 6/2013 |
| WO | 20140011925 | 1/2014 |
| WO | 20140140635 | 9/2014 |
| WO | 20150155521 | 10/2015 |
| WO | WO 2015/144916 | 10/2015 |

OTHER PUBLICATIONS

Vymazal et al. 1996 The relation between brain iron and NMR relaxation times: An in vitro study. Magn Reson Med. 1996; 35:56-61.
Wood, et al. MRI R2 and R2* mapping accurately estimates hepatic iron concentration in transfusion-dependent thalassemia and sickle cell disease patients. Blood. 2005; 106:1460-5).
Clinical NMR Group. "Magnetic resonance imaging of parenchymal liver disease: a comparison with ultrasound, radionuclide scintigraphy and X-ray computed tomography." Clinical Radiology 38.5 (1987): 495-502.
International Search Report Application No. PCT/GB2014/050815 dated Aug. 19, 2014, 14 pages.
Ghugre et al., "Relaxivity-iron calibration in hepatic iron overload: Probing underlying biophysical mechanisms using a Monte Carlo model", Magnetic Resonance in Medicine, vol. 65, No. 3, Mar. 2011, pp. 837-847.
Cheng et al., "Practical medical applications of quantitative MR relaxometry", Journal of Magnetic Resonance Imaging: JMRI, vol. 36, No. 4, Oct. 2012, pp. 805-824.
Mackay et al., "In Vivo Visualization of Myelin Water in Brain by Magnetic Resonance", Magnetic Resonance in Medicine, vol. 32, No. 6, Jun. 1, 1994, pp. 673-677.
Ghugre et al., "Mechanisms of tissue-iron relaxivity: nuclear magnetic resonance studies of human liver biopsy specimens", Magnetic Resonance in Medicine, vol. 54, No. 5, Nov. 2005.
Van Werven et al. Assessment of Hepatic Steatosis in Patients Undergoing Liver Resection: Comparison of US, CT, T1-weighted Dual-Echo MR Imaging,and Point-resolved 1 H MR Spectroscopy, Radiology: vol. 256: No. 1—Jul. 2010.
McPherson et al. Magnetic resonance imaging and spectroscopy accurately estimate the severity of steatosis provided the stage of fibrosis is considered. Journal of Hepatology, vol. 51, Issue 2, Aug. 2009, pp. 389-397.
RM SSE, http://www.uta.edu/faculty/sawasthi/Statistics/glosr.html Nov. 2007.
Aisen, et al. Detection of liver fibrosis with magnetic cross-relaxation. Magn Reson Med. 1994; 31:551-6).
Alanen et al., Acta. Radiol., Jul. 1998; 39 (4): 434-9. "MR and magnetisation transfer imaging in cirrhotic and fatty livers."
Bacic et al. NMR study of water exchange across the hepatocyte membrane. Magn Reson Imaging 1989; 7:411-416.
Banerjee et al "Multiparametric Magnetic Resonance for the non-invasive diagnosis of liver disease." J Hepatol. (2014) 60(1):69-77.
Bohte, A. E., A. de Niet, et al. "Non-invasive evaluation of liver fibrosis: a comparison of ultrasound-based transient elastography and MR elastography in patients with viral hepatitis B and C." Eur Radiol 24(3): 638-48. Oct. 2013.
Bosch, J., J. G. Abraldes, et al. (2009). "The clinical use of HVPG measurements in chronic liver disease." Nat Rev Gastroenterol Hepatol 6(10): 573-582.
Bravo, A. A.,et al. (2001). "Liver Biopsy." New England Journal of Medicine 344(7): 495-500.
Bredella Ma, et al J Comput Assist Tomogr. May-Jun. 2010;34(3):372-6. Breath-hold 1H-magnetic resonance spectroscopy for intrahepatic lipid quantification at 3 Tesla.
British Liver Trust, 2006 Alcohol and liver disease. Ringwood: British Liver Trust, 2006.
Chamuleau, et al. Is the magnetic resonance imaging proton spin-lattice relaxation time a reliable noninvasive parameter of developing liver fibrosis? Hepatology. 1988; 8:217-21.
Colecchia A, et al Measurement of spleen stiffness to evaluate portal hypertension and the presence of esophageal varices in patients with HCV-related cirrhosis. Gastroenterology. Sep. 2012;143(3):646-54.
Ekstedt M, et al. Hepatology 2006; 44: 865. Long-term follow-up of patients with NAFLD and elevated liver enzymes.
El Badry AM et al, Annals of Surgery 250(5), Nov. 2009, 691-697. Assessment of Hepatic Steatosis by Expert Pathologists: The End of a Gold Standard.
Ferreira VM, et al Non-contrast T1-mapping detects acute myocardial edema with high diagnostic accuracy: a comparison to T2-weighted cardiovascular magnetic resonance .J Cardiovasc Magn Reson 2012;14:42.
Fleming, Kate M., et al. "Abnormal liver tests in people aged 75 and above: prevalence and association with mortality." Alimentary pharmacology & therapeutics 34.3 (2011): 324-334.
Ghugre et al. Multi-field behavior of Relaxivity in an Iron-rich environment. Proc Intl Soc Mag Reson Med. 2008; 16:644).
Goldberg, et al. Hepatic cirrhosis: magnetic resonance imaging. Radiology. 1984; 153:737-9.

(56) References Cited

OTHER PUBLICATIONS

Graham and Henkelman Understanding pulsed magnetisation transfer. J Magn Reson Imaging 1997; 7:903-912.
Guo H. et al., J Magn Reson Imaging, Aug. 2009; 30(2):394-400. Myocardial T2 Quantitation in Patients With Iron Overload at 3 Tesla.
Henninger, et al. Evaluation of MR imaging with T1 and T2* mapping for the determination of hepatic iron overload. Eur Radiol. 2012; 22:2478-86.
Heye, et al. MR relaxometry of the liver: significant elevation of T1 relaxation time in patients with liver cirrhosis. Eur Radiol. 2012; 22:1224-32.
Hilt PJ Thesis, Quantification of Cardiac Longitudinal Relaxation (T1) AT 3.0 T During Normal and Hyperoxic Breathing Conditions, Aug. 2008.
Hines CDG et al. Radiology; 254: 1; Jan. 2010 Quantification of Hepatic Steatosis with 3T MR Imaging: Validation in ob/ob Mice.
Ishak et al., Histological grading and staging of chronic hepatitis. J Hepatol. 1995; 22:696-9.
Janiec DJ et al, Obes Surg. Apr. 2005;15(4):497-501. Histologic variation of grade and stage of non-alcoholic fatty liver disease in liver biopsies.
Keevil, et al. Non-invasive assessment of diffuse liver disease by in vivo measurement of proton nuclear magnetic resonance relaxation times at 0.08 T. Br J Radiol. 1994; 67:1084-1087).
Kim, et al. Quantitative evaluation of liver cirrhosis using T1 relaxation time with 3 tesla MRI before and after oxygen inhalation. J Magn Reson Imaging. 2012; 36:405-10.
Klasen J, et al Diffusion-weighted imaging (DWI) of the spleen in patients with liver cirrhosis and portal hypertension. Magn Reson Imaging. Sep. 2013;31(7):1092-6.
Li Zhou et al PLOS One (2013) 8(12): e83697.
Merkel, C. and S. Montagnese "Hepatic venous pressure gradient measurement in clinical hepatology." Digestive and Liver Disease 43(10): 762-767.
Messroghli DR et al, 2007 Optimization and Validation of a Fully-Integrated Pulse Sequence for Modified Look-Locker Inversion-Recovery (MOLLI) T1 Mapping of the Heart, Journal of Magnetic Resonance Imaging 26:1081-1086, 2007.
Messroghli DR, et al, 2004 Magn Reson Med 2004; 52:141-146. Modified Look-Locker inversion recovery (MOLLI) for high-resolution T1 mapping of the heart.
Nedredal GI et al Portal hypertension correlates with splenic stiffness as measured with MR elastography. J Magn Reson Imaging. Jul. 2011;34(1):79-87.
Patch, D., et al. (1999). "Single portal pressure measurement predicts survival in cirrhotic patients with recent bleeding." Gut 44(2): 264-9.
Perello A, et al (1999). "Wedged hepatic venous pressure adequately reflects portal pressure in hepatitis C virus-related cirrhosis." Hepatology 30(6): 1393-1397.
Piechnik SK, et al, 2010 J Cardiovasc Magn Reson. Nov. 19, 2010;12:69. Shortened Modified Look-Locker Inversion recovery (ShMOLLI) for clinical myocardial T1-mapping at 1.5 and 3 T within a 9 heartbeat breathhold.
Piechnik SK et al, 2013 "Normal variation of magnetic resonance T1 relaxation times in the human population at 1.5 T using ShMOLLI." J Cardiovasc Magn Reson 15: 13.
Regev A et al, Am J Gastroenterol. Oct. 2002; 97(10):2614-8. Sampling error and intra-observer variation in liver biopsy in patients with chronic HCV infection.
Rincon D et al. (2007). "Prognostic value of hepatic venous pressure gradient for in-hospital mortality of patients with severe acute alcoholic hepatitis." Aliment Pharmacol Ther 25(7): 841-8.
Ripoll C et al. (2005). "Influence of hepatic venous pressure gradient on the prediction of survival of patients with cirrhosis in the MELD Era." Hepatology 42(4): 793-801.
Rohrer et al., Comparison of magnetic properties of MRI contrast media solutions at different magnetic field strengths. Invest Radiol. 2005; 40:715-24.

Siegelman E S, MR imaging of diffuse liver disease. Hepatic fat and iron pp. 347-365. Magnetic resonance imaging clinics of North America, vol. 5, May 1997, United States.
St Pierre, et al. Noninvasive measurement and imaging of liver iron concentrations using proton magnetic resonance. Blood. 2005; 105:855-61.
Standish RA et al Gut. Apr. 2006;55(4):569-78. An appraisal of the histopathological assessment of liver fibrosis.
Thomsen, et al. Prolonged T1 in patients with liver cirrhosis: An in vivo MRI study. Magn Reson Imaging. 1990; 8:599-604.
Varghese T et al. "Elastographic imaging using a handheld compressor." Ultrason Imaging. Jan. 2002;24(1):25-35.
Versluis et al., Detection of cerebral microbleeds: Physical principles, technical aspects and new developments. In: Cerebral Microbleeds ed. Werring DJ. Cambridge University Press, 2011; pp. 13-21.
Koenig, Seymour H., and Rodney D. Brown. "Relaxometry of tissue." Encyclopedia of Magnetic Resonance, (2007): 1-13.
Bieri and Scheffler, Fundamentals of balanced steady state free precession MRI, journal of magnetic resonance imaging, 38, 2-11, 2013.
Burt et al, Myocardial T1 mapping: techniques and potential applications, Cardiac imaging, 34(2), 377-395, 2014.
Chundru et al, MRI of diffuse liver disease: the common and uncommon etiologies, diagnostic and interventional radiology, 2013.
De Miguel M H et al, "Evaluation of quantitative magnetic resonance imaging as a noninvasive technique for measuring renal scarring in a rabbit model of antiglomerular basement membrane disease.", Journal of the American Society of Nephrology : JASN May 1994, (May 1994), vol. 4, No. 11, pp. 1861-1868.
Fischer R et al., "Assessment of iron stores in children with transfusion siderosis by biomagnetic liver susceptometry", Hematology 1999;60(4):289-299.
Hamilton et al., "Effect of PRESS and STEAM sequences on magnetic resonance spectroscopic liver fat quantification", J Magn. Reson. Imaging 2009; 30:145-152.
Hamilton G, Middleton MS, Hooker JC, Haufe WM, Forbang NI, Allison MA, et al. In vivo breath-hold (1) H MRS simultaneous estimation of liver proton density fat fraction, and T1 and T2 of water and fat, with a multi-TR, multi-TE sequence. J Magn Reson Imaging [Internet]. Jun. 25, 2015 [cited Nov. 19, 2015];42(6):1538-43.
Hamilton G, Yokoo T, Bydder M, Cruite I, Schroeder ME, Sirlin CB, et al In vivo characterization of the liver fat 1H MR spectrum. NMR Biomed. 2011;24(7):784-90.
Hargreaves, Rapid Gradient-Echo Imaging, Journal of Magnetic Resonance Imaging, 36,1300-1313, 2012.
Hines CDG, Yu H, Shimakawa A, McKenzie CA, Brittain JH, Reeder SB T1 independent, T2* corrected MRI with accurate spectral modeling for quantification of fat: Validation in a fat-water-SPIO phantom. J Magn Reson Imaging. 2009;30(5):1215-22.
Idilman IS et al., "Hepatic steatosis: quantification by proton density fat fraction with MR imaging versus liver biopsy", Radiology 2013;267:767-775.
Kellman et al. J. Cardiovascular Mag. resonance (2015) 17:3.
Kellman P. et al., "Influence of Off-resonance in myocardial T1-mapping using SSFP based MOLLI method", J. Cardiovasc. Magn. Reson. Jul. 22, 2013;15:63.
Kim et al, Myocardial T1 and T2 mapping: techniques and clinical applications, Korean journal of radiology, 18(1), 113-131, 2017.
Larmour et al., "Characterization of T1 bias in skeletal muscle from fat in MOLLI and SASHA pulse sequences: Quantitative Fat-Fraction imaging with T1 mapping", Magnetic Resonance in Medicine 77:237-249 (2017).
Ling C R et al., "Changes in NMR relaxation time associated with local inflammatory response", Physics in Medicine and Biology, Institute of Physics Publishing, Bristol GB, (Jun. 1, 1982), vol. 27, No. 6, pp. 853-860.
Ma et al, Magnetic Resonance Fingerprinting, Nature, 495, 187-193, 2013.
Mozes FE, et al., "Influence of fat on liver T1 measurements using modified Look-Locker inversion recovery (MOLLI) methods at 3T", J. Magn. Reson. Imaging. Jan. 13, 2016; 44:105-111.

(56) References Cited

OTHER PUBLICATIONS

Sahani, The Oncologist (2004):9:385-397.

Sirlin C et al., "Magnetic Resonance Imaging Quantification of Liver Iron", Magn. Reson. Imaging Clin. N. Am. 2012;18 (3):359.

Squires et al., J Pediatr. May 2006;148(5):652-658).

Storey P et al., "R2* imaging of transfusional iron burden at 3T and comparison with 1.5T", J. Magn. Reson. Imaging 2007;25:540-547).

Szczepaniak LS et al., "Magnetic resonance spectroscopy to measure hepatic triglyceride content: prevalence of hepatic steatosis in the general population" Am. J. of Physiol. Endocrinol. Metab. 2005;288:E462-468.

Tang A et al. "Nonalcoholic Fatty Liver Disease: MR Imaging of Liver Proton Density Fat Fraction to Assess Hepatic Steatosis" Radiology 2013;267:422-431.

Tunnicliffe EM, Banerjee R, Pavlides M, Neubauer S, Robson MD., model for hepatic fibrosis: the competing effects of cell loss and iron on shortened modified Look-Locker inversion recovery T 1 (shMOLLI-T 1) in the liver. J Magn Reson Imaging [Internet]. Jul. 2016 [cited Sep. 16, 2016].

Wang et al., Factors influencing flip angle mapping in mri: rf pulse shape, slice-select gradients, off-resonance excitation, and bo inhomogeneities, magnetic resonance in medicine, 56, 463-468, 2006.

Wood J., "Impact of Iron Assessment by MRI", AHS Education Book, Dec. 10, 2011; 1:443-450.

Yu H, McKenzie CA, Shimakawa A, Vu AT, Brau ACS, Beatty PJ, et al., Multiecho reconstruction for simultaneous water-fat decomposition and T2* estimation. J Magn Reson Imaging [Internet]. Oct. 2007 [cited Mar. 5, 2015];26 (4):1153-61.

European Office Action for Application No. 14 711 591.9-1657 dated Feb. 14, 2017.

European Office Action for Application No. 14 711 591.9-1657 dated Nov. 30, 2017.

Japanese Office Action for Application No. 2015-562331 dated Jan. 18, 2018 w/English translation.

Singaporean Office Action for Application No. 11201507628W dated Nov. 15, 2017.

SG Written Opinion for Application No. 11201507628W dated Dec. 5, 2016.

Singaporean Office Action for Application No. 11201507628W dated Apr. 3, 2017.

United Kingdom Office Action for Application No. 1404628.8 dated Aug. 1, 2017.

United Kingdom Office Action for Application No. 1304728.7 dated Sep. 17, 2013.

United Kingdom Office Action for Application No. 1404628.8 dated Apr. 18, 2017.

United Kingdom Office Action for Application No. 1404628.8 dated Aug. 20, 2014.

United Kingdom Office Action for Application No. 1404628.8 dated Jun. 30, 2017.

United Kingdom Office Action for Application No. 1404628.8 dated Sep. 7, 2017.

Mescam et al. "Coupling texture analysis and physiological modeling for liver dynamic MRI interpretation" 2007 Annual International Conference of the IEEE Engineering in medicine and biology conference (EMBC '07) Lyon, France, 22-26; Aug. 2007 pp. 4223-4226.

Mescam et al., "Multiscale model of liver DCE-MRI towards a better understanding of tumor complexity" IEEE Transactions on medical imaging, IEEE Service Center, Piscataway, NJ, US, vol. 5, No. 3, Mar. 1, 2010, pp. 699-707.

Sommer et al. "Contrast agents as biological markers in magnetic resonance imaging of the liver: conventional and new approaches", Abdominal Imaging, Springer-Verlag, NE, vol. 37, No. 2, Apr. 24, 2011, pp. 164-179.

* cited by examiner

METHOD AND SYSTEM FOR DETERMINING A CORRECTED VALUE OF MAGNETIC RESONANCE RELAXOMETRY DATA OF A SUBJECT'S VISCERAL TISSUE FOR EXTRACELLULAR FLUID BASED ON A NORMAL IRON CONTENT FOR THE VISCERAL TISSUE

CROSS-REFERENCE TO RELATED APPLICATIONS

This application is the National Stage of International Application No. PCT/GB2014/050815, filed 14 Mar. 2014, which claims the benefit of and priority to GB application 1304728.7, filed 15 Mar. 2013, the contents of all of which are incorporated by reference as if fully set forth herein.

TECHNICAL FIELD

The present disclosure generally relates to medical imaging and, more particularly, relates to systems and methods for performing processing of magnetic resonance imaging of the liver and other organs which may be useful in the diagnosis of fibrosis in the liver and other organs.

BACKGROUND

As many as one in ten adults in the UK have some form of liver disease (British Liver Trust. Alcohol and liver disease. Ringwood: British Liver Trust, 2006). Liver disease is currently the fifth most common cause of mortality for both men and women (Department of Health. Quality Strategy Team Report on Liver Disease: A seeping study into the nature and burden of the disease, 2006). However, whilst the mortality rates for the other four major causes of death are falling, the trend for liver disease is rising in both sexes at an alarming rate and there has been a five-fold increase in the prevalence of liver cirrhosis in the last 30 years. The current childhood obesity epidemic, increasing alcohol misuse and viral hepatitis are all contributing to this. The problem with liver disease is that often symptoms of the disease are not apparent until the disease reaches an advanced stage. Thus, there is a pressing need for a reliable diagnostic tool for liver disease to identify early disease and to target therapies to those patients that may benefit (e.g., antiviral therapy in progressive hepatitis C, weight reduction surgery in fatty liver disease).

The current accepted practice, or "gold standard", for diagnosing liver disease is an ultrasound-guided liver biopsy. This is less than ideal as there is a small but significant complication risk (1:1000 of severe bleeding, especially in coagulopathic patients). Furthermore, only 0.002% of the liver is examined, and there is great intraand inter-observer variability in histological interpretation (see, e.g., Sampling error and intra-observer variation in liver biopsy in patients with chronic HCV infection. Regev A et al, Am J Gastroenterol. 2002 October; 97(10):2614-8. Histologic variation of grade and stage of non-alcoholic fatty liver disease in liver biopsies. Janiec O J et al, Obes Surg. 2005 April; 15(4):497-501. Assessment of Hepatic Steatosis by Expert Pathologists: The End of a Gold Standard. El Badry A M et al, Annals of Surgery 250(5), November 2009, 691-697).

A relatively high proportion of patients referred for liver biopsy have high liver iron. As an example, approximately one-third of the patients recruited to our study below had high liver iron. Fibrosis cannot be assessed accurately in this population using a non-invasive imaging procedure such as T1 mapping without some kind of correction.

Accordingly, there is a need to address the aforementioned deficiencies and inadequacies.

SUMMARY

Briefly described, systems and methods for evaluating liver fibrosis/inflammation in the presence of elevated iron are provided. Our systems and methods may involve analysing magnetic resonance (M R) data for diagnosis of liver fibrosis and/or inflammation. In particular, the present disclosure enables assessment of liver fibrosis/inflammation in patients using magnetic resonance (MR) relaxometry for measuring one or more characteristic relaxation time or times, particularly in the presence of high liver iron.

In magnetic resonance (MR) imaging, tissue contrast is generated by a combination of intrinsic tissue properties such as spin-lattice (T1) and spin-spin (T2) relaxation times, and extrinsic properties such as imaging strategies and settings. Signal intensity in conventional MR images is displayed on an arbitrary scale, and thus is not adequate for direct comparisons. T1 relaxation times depend on the composition of tissues. T1 relaxation times exhibit characteristic ranges of normal values at a selected magnetic field strength. Deviation from established ranges can thus be used to quantify the effects of pathological processes.

We have discovered that using the present analysis method to process MR relaxometry data of liver tissue can reliably show differences in extracellular fluid (ECF) content in the liver and thereby allow quantification of the degree of liver fibrosis and thus serve as a biomarker for liver disease, even in the presence of high liver iron. In particular, we have developed a new approach to interpreting magnetic resonance relaxometry (for example T1 and T2* mapping) of liver disease. T1 mapping is useful for assessing fibrosis, but in the presence of iron, this relationship is disrupted.

We provide a model of the liver consisting of at least two compartments, with variable amounts of iron and extracellular fluid, and then simulate its behaviour under the exact T1 mapping MRI sequence and reconstruction method that is used in vivo. These simulation results can be used, for example, as a look-up table, or the simulation can be run iteratively on a per-patient basis. Given the known iron (for example from T2* mapping) and measured T1, we can then infer the patient's extracellular fluid fraction, and thus the level of hepatic fibrosis/inflammation.

One embodiment of the present systems and methods comprises: obtaining a measurement of relaxometry data of a subject's liver for extracellular fluid; determining an iron content for the liver; simulating a measurement of the subject's liver for extracellular fluid for the determined iron content; comparing the measurement of the subject's liver for extracellular fluid to the simulated measurement of the subject's liver for extracellular fluid; and determining from said comparison a value of extracellular fluid in the subject's liver based on a normal iron content for the liver.

Another embodiment is a system or apparatus comprising at least one computing device and at least one application executable in the at least one computing device, the at least one application comprising logic that obtains a measurement of relaxometry data of a subject's liver for extracellular fluid; measures the liver for iron content; simulates a measurement of the subject's liver for extracellular fluid for the determined iron content; compares the measurement of the subject's liver for extracellular fluid to the simulated measurement of the subject's liver for extracellular fluid; and determines from said comparison a value of extracellular fluid in the subject's liver based on a normal iron content for the liver.

Another embodiment is a carrier bearing software comprising instructions for configuring a processor to carry out the steps of obtaining a measurement of relaxometry data of a subject's liver for extracellular fluid, determining an iron content for the liver, simulating a measurement of the subject's liver for extracellular fluid for the determined iron content; comparing the measurement of the subject's liver for extracellular fluid to the simulated measurement of the subject's liver for extracellular fluid, and determining from said comparison a value relating to the extracellular fluid in the subject's liver based on a normal iron content for the liver.

The methods, systems, apparatus and carriers of the present invention may also be applied to other organs or visceral tissues where biopsy is not routine or possible, for example the spleen and heart.

Therefore in a further embodiment the invention provides a method for processing MR relaxometry data of visceral tissue comprising: obtaining a measurement of relaxometry data of a subject's visceral tissue for extracellular fluid; determining an iron content for the visceral tissue; simulating a measurement of the subject's visceral tissue for extracellular fluid for the determined iron content; comparing the measurement of the subject's visceral tissue for extracellular fluid to the simulated measurement of the subject's visceral tissue for extracellular fluid; and determining from said comparison a value of extracellular fluid in the subject's visceral tissue based on a normal iron content for the visceral tissue.

Another embodiment is a system or apparatus comprising at least one computing device and at least one application executable in the at least one computing device, the at least one application comprising logic that obtains a measurement of relaxometry data of a subject's visceral tissue for extra-cellular fluid; measures the visceral tissue for iron content; simulates a measurement of the subject's visceral tissue for extracellular 20 fluid for the determined iron content; compares the measurement of the subject's visceral tissue for extracellular fluid to the simulated measurement of the subject's visceral tissue for extracellular fluid; and determines from said comparison a value of extracellular fluid in the subject's visceral tissue based on a normal iron content for the visceral tissue.

Another embodiment is a carrier bearing software comprising instructions for configuring a processor to carry out the steps of obtaining a measurement of relaxometry data of a subject's visceral tissue for extracellular fluid, determining an iron content for the visceral tissue, simulating a measurement of the subject's visceral tissue for extracellular fluid for the determined iron content; comparing the measurement of the 30 subject's visceral tissue for extracellular fluid to the simulated measurement of the subject's visceral tissue for extracellular fluid, and determining from said comparison a value relating to the extracellular fluid in the subject's visceral tissue based on a normal iron content for the visceral tissue.

The visceral tissue may be any internal organ of the body, preferably liver, heart or spleen, most preferably liver.

Any one or more of the embodiments can further include determining a corrected measured value of extracellular fluid from the comparison. The presence or absence of liver fibrosis can be determined from the measurements and comparison, as well as the extent of fibrosis.

In any one or more of the embodiments, the subject's liver can be measured using a medical imaging device, such as a magnetic resonance (MR) scanner. For example, a medical imaging device, such as a magnetic resonance imaging (MRI) device may be provided and a subject, such as a patient, positioned in association with the medical imaging device. The measurement of relaxometry data may be obtained using the medical imaging device. In one or more aspects an MR scanner can be used, for example, to measure one or more characteristic relaxation time or times in the liver tissue. The liver can be measured for extracellular fluid content using an MR scanner. The liver can also be measured for iron content using an MR scanner. In particular, the subject's liver can be measured for extracellular fluid using MR relaxometry, for example, T1 mapping.

In any one or more of the embodiments, the subject's liver can also be measured for iron content using one or more of T2 mapping, T2* mapping, measuring one or more blood biomarkers, such as ferritin, transferrin, transferrin saturation, hepcidin, soluble transferrin receptor (sTfR) index (sTfR/log ferritin), or MR spectroscopy. For example, the width of the 1H MRS spectra can indicate higher than normal iron loads.

In any one or more embodiments, the measurement of the subject's liver for extracellular fluid can include obtaining a T1 map of the liver, the simulation can include determining a predicted measured T1 map associated with a particular extracellular fluid fraction of the liver for the iron content determined and the comparison can include comparing the measured T1 to the predicted measured T1. A corrected T1 measurement can then be determined based on a normal iron content for the liver. The simulation can include multi-compartment modeling of various fractions of extracellular fluid in the liver and the impact of iron content in the liver on both the intra- and extracellular relaxation times. The simulation can also include simulating a predicted measurement of the liver for various fractions of extracellular fluid and the impact of iron content on both the intra- and extracellular fluid relaxation times in combination with a simulation of an imaging sequence, for example an imaging sequence involving T1 mapping. The simulation may involve a Bloch equation simulation.

In any one or more of the embodiments any T1 mapping method may be applied for acquiring M R relaxometry measurements or data, as long as the details for the T1 mapping sequence are known. Suitable T1 mapping methods include, but are not limited to, the spin-lattice T1 mapping that can be performed using repeated inversion recovery (IR) experiments. For example, a modified Look Locker inversion (MOLLI) recovery pulse sequence can be performed. The MOLLI sequence is generally described in Messroghli D R, Radjenovic A. Kozerke S, Higgins D M, Sivananthan M U, Ridgway J P. Modified Look-Locker inversion recovery (MOLLI) for high resolution T1 mapping of the heart. Magn Reson Med 2004; 52:141-146 which is incorporated by reference as if fully set forth herein. In one or more further embodiments, among others, where a shortened breath-hold is desired, the spin-lattice (T1) mapping can be performed using a shortened modified Look Locker inversion recovery (Sh-MOLLI) sequence. The Sh-MOLLI sequence is generally described in Piechnik S K, Ferreira V M, Daii'Armellina E, Cochlin L E, Greiser A, Neubauer S, Robson M D., Shortened Modified Look-Locker Inversion recovery (ShMOLLI) for clinical myocardial T1-mapping at 1.5 and 3 T within a 9 heartbeat breath hold, J Cardiovasc Magn Reson. 2010 Nov. 19; 12:69, which is incorporated by reference as if fully set forth herein. It can also be applied to the family of saturation recovery T1-mapping methods, or variable flip angle T1-mapping methods.

Other systems, methods, features, and advantages of the present disclosure for performing processing of imaging of the liver or assisting in the diagnosis of liver fibrosis or inflammation will be or become apparent to one with skill in the art upon examination of the following drawings and detailed description. It is intended that all such additional systems, methods, features, and advantages be included within this description, be 30 within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1 A-B show the impact of correcting T1 on the correlation with Ishak score, with patients subdivided into normal and abnormal iron groups. A) The correlation between Ishak score and measured (uncorrected) T1 shows that, for patients with iron overload, the T1 is often markedly decreased compared to the expected value from patients with normal iron given the Ishak score. B) Correcting the T1 improves the agreement between normal and abnormal iron patients.

DETAILED DESCRIPTION

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

Medical imaging, for example magnetic resonance imaging (MRI), can be used to measure tissue characteristics that can in combination help to determine the presence and severity of liver disease, including in particular, liver fibrosis. MRI can be a powerful tool in the diagnosis of liver disease. In recent years the use of relaxometry, the measurement of the characteristic relaxation times in liver tissue, has become more widespread, due to the sensitivity of T2 and T2* to iron accumulation in the liver (St Pierre, et al. Noninvasive measurement and imaging of liver iron concentrations using proton magnetic resonance. Blood. 2005; 105:855-61 and Wood, et al. MRI R2 and R2* mapping accurately estimates hepatic iron concentration in transfusion-dependent thalassemia and sickle cell disease patients. Blood. 2005; 106:1460-5).

In the nineties, some groups identified elevated T1 in the livers of patients with cirrhosis (Thomsen, et al. Prolonged T1 in patients with liver cirrhosis: An in vivo MRI study. Magn Reson Imaging. 1990; 8:599-604 and Keevil, et al. Non-invasive assessment of diffuse liver disease by in vivo measurement of proton nuclear magnetic resonance relaxation times at 0.08 T. Br J Radiol. 1994; 67:1084-1087), but this did not gain widespread acceptance, perhaps in part because of conflicting experimental data (Goldberg, et al. Hepatic cirrhosis: magnetic resonance imaging. Radiology. 1984; 153:737-9; Chamuleau, et al. Is the magnetic resonance imaging proton spin-lattice relaxation time a reliable noninvasive parameter of developing liver fibrosis? Hepatology. 1988; 8:217-21; Aisen, et al. Detection of liver fibrosis with magnetic crossrelaxation. Magn Reson Med. 1994; 31:551-6), and a lack of easily applied in-vivo T1-mapping methods.

More recently, with the development of robust, single breath-hold T1 mapping techniques (Piechnik, et al. Shortened Modified Look-Locker Inversion recovery (ShMOLLI) for clinical myocardial T1-mapping at 1.5 and 3 T within a 9 heartbeat breathhold. J Cardiovasc Magn Reson. 2010 12:69), interest in T1-mapping of the liver in patients with cirrhosis has increased again (Heye, et al. MR relaxometry of the liver: significant elevation of T1 relaxation time in patients with liver cirrhosis. Eur Radiol. 2012; 22:1224-32 and Kim, et al. Quantitative evaluation of liver cirrhosis using T1 relaxation time with 3 tesla MRI before and after oxygen inhalation. J Magn Reson Imaging. 2012; 36:405-10). However, these studies have excluded patients with iron overload. One study (Henninger, et al. Evaluation of MR imaging with T1 and T2* mapping for the determination of hepatic iron overload. Eur Radiol. 2012; 22:2478-86) has addressed the additional information that can be gained by combining T2* and T1 measurements, but only qualitatively (presence/absence of iron overload or fibrosis).

Using MR relaxometry to measure one or more characteristic time or times in the liver tissue, for example, using T1 mapping of the liver, can reliably show differences in extracellular fluid (ECF) content. Higher T1 relaxation time determined from T1 mapping of the liver for extracellular fluid measurement is an indication of fibrosis in the liver. A higher T1 relaxation time can indicate a higher degree of hepatic fibrosis or active hepatitis. For example, we observed that liver T1 values were elevated in patients with normal liver iron and increased fibrosis, measured by Ishak score, indicating a relationship between T1 values and the presence of extracellular fluid and liver fibrosis. See e.g., FIG. 1A. Thus, in liver tissue with normal iron content, T1 mapping of the organ can reliably show differences in extracellular fluid content and thereby allow quantification of the degree of liver fibrosis/inflammation, for example by defining T1 ranges corresponding to normal, mild (1-2), moderate (3-4) or severe (5-6) fibrosis on the Ishak scale.

We have discovered, however, that elevated liver iron, or iron overload, can alter the T1 relaxation time and its measurement. Mild iron overload is relatively common in the general population, and higher still in patients with suspected liver disease. The most important causes of iron overload are hereditary hemochromatosis (HHC), a highly prevalent genetic disease with autosomal dominant heritability, transfusion iron overload, and chronic liver disease. Iron overload tends to lower T1 relaxation time and, through its effects on T2 and T2*, also affect the precision of its measurement using a particular sequence and, thereby, cause the measured T1 relaxation time to underreport, for example, extracellular fluid measurement. Iron overload commonly causes liver cirrhosis if left untreated, so the two commonly coexist.

Measuring iron content allows correcting for underreporting by T1 values when iron overload is present. For example, in liver tissue with excess iron content, T2* mapping can determine the degree of iron overload. Iron overload of the liver is toxic and causes fibrosis, and causes a reduced T2* value. The T1 value can be corrected in patients with reduced T2* to still enable assessment for fibrosis.

Other methods can be used to measure iron content besides T2* mapping. Suitable methods also include T2 mapping (StPierre et al., Noninvasive measurement and imaging of liver iron concentrations using proton magnetic resonance. Blood. 2005; 105:855-61, which is incorporated by reference as if fully set forth herein), and measuring one or more blood biomarkers, such as ferritin, transferrin, transferrin saturation, hepcidin, soluble transferrin receptor (sTfR) index (sTfR/log ferritin). MR spectroscopy can also be used to measure iron content and, thus, iron overload. For example, the width of the 1H MRS spectra can indicate higher than normal iron loads.

Accurate quantification of the impact of iron on the measurement of T1 in theliver can provide for rapid noninvasive diagnosis of the type and/or severity of liver fibrosis regardless of liver iron content. To enable a more quantitative approach to the impact of iron on the measurement of T1 in the liver, we provide a novel multiple compartment biophysical model of the microscopic environment of the water in the liver.

The presence of paramagnetic iron-containing compounds in the body causes local, microscopic magnetic field variations. These field inhomogeneities not only cause more rapid decoherence of magnetization in the transverse plane, but also increase the spectral weight at the Larmor frequency, thus reducing the T1 relaxation time. Measured T1 is also affected by the partial volume of different tissues within an imaging voxel, for example, a high proportion of free fluid in a voxel will lead to a longer T1. These competing effects can limit the use of T1-mapping alone to quantify either extracellular fluid (ECF) or iron.

Figure 2:
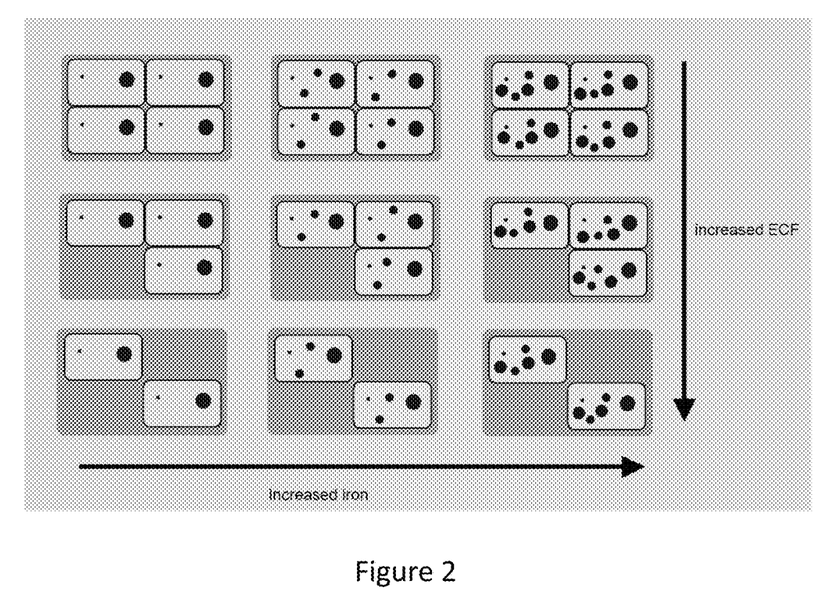
FIG. 2 schematically depicts the changes in the two cellular components of an exemplary model of our present disclosure, extracellular fluid (ECF) fraction (which increases as cells die) and iron overload (iron is primarily stored intracellularly).

In an example of a two-compartment model, shown in FIG. 2, compartments correspond to intra- and extracellular fluid, the proportions of which can be varied. The quantity of iron in the cells can also be varied, corresponding to different hepatic iron contents. Other compartments could also be included, for example fat. The magnetic resonance behaviour of the water in these compartments is modeled using knowledge of the field strength of the MR relaxometry, and exact details T1-mapping pulse sequence, which could be, for example, any of inversion recovery, saturation recovery or variable flip angle T1-mapping method. The model can be, for example, a full Bloch simulation. The output of this model is the dependence of the measured T1 on the different variables, for example extracellular fluid fraction and iron in the case of one two-compartment model. If the iron has been independently measured, for example using T2* mapping, it is then possible to assess the extracellular fluid fraction given the hepatic iron content and measured T1, and hence correct the measured T1 for an individual patient, as if the patient's iron levels were normal.

Figure 3:
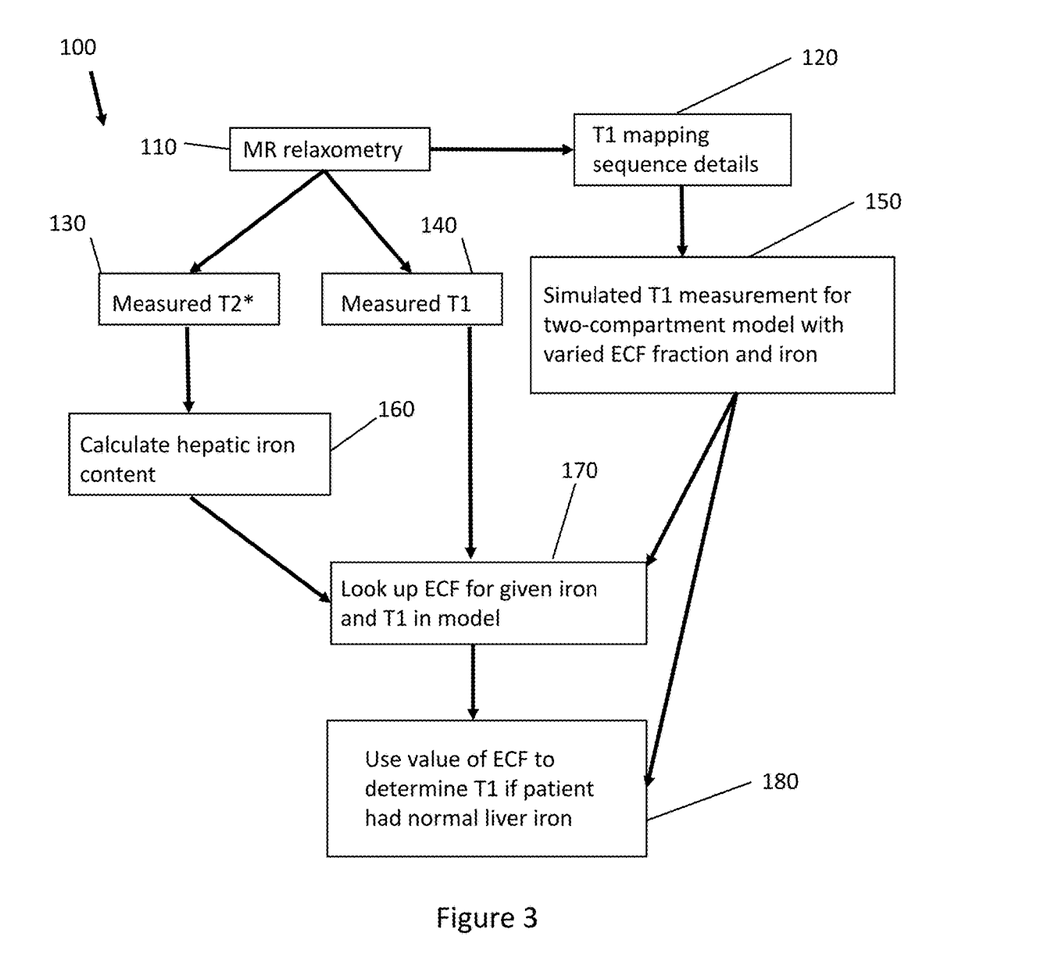
FIG. 3 depicts a flow chart for one non-limiting embodiment for performing the magnetic (MR) diagnosis of a liver disclosed herein.

One embodiment of the present systems and methods for performing magnetic resonance (MR) diagnosis of a liver is illustrated in FIG. 3, which depicts a flowchart 100 for performing imaging assessment of a liver taking into effect the presence of iron in the liver on MR relaxometry measurements, for example, T1 measurements.

MR relaxometry data 110 are obtained of a subject's liver. The relaxometry data may be for extracellular fluid in the liver tissues. A subject may be a mammalian subject, including in particular a human subject. The relaxometry data may include the details of the T1 mapping sequence used 120. Included in this MR relaxometry data is a measured T2* 130 and measured T1 140, in the form of maps or values determined from larger regions of interest in the tissue.

Hepatic iron content can be determined 140 from the measured T2*. A non-limiting example of how hepatic iron content (HIC) can be determined is provided in the Methods and Examples section below. Alternatively, T2 mapping could be used. Another method is to measure dry weight iron from a separate liver biopsy-normal liver typically has less than 3 mmols per 100 g of liver tissue.

We simulate a measurement 150 of the subject's liver for extracellular fluid (ECF) for a given T1 measurement sequence. For example, we can employ a multiple compartment biophysical model of the microscopic environment of water in the liver. At least two compartments can be adopted, one corresponding to intra-cellular fluid and one to extracellular fluid, the proportions of which can be varied. Additionally, the quantity of iron in the cells can also be varied in the simulation. The magnetic resonance behaviour of the water in the compartments can then be modeled using, for example, the relaxation characteristics of water in the different compartments, equations such as Bloch equations, knowledge of the pulse sequence employed to obtain the relaxometry data 110, the method used to calculate the T1 map, and the biophysical model adopted, to simulate a T1 measurement. The impact of the variable fraction of extracellular fluid and iron content on the relaxation characteristics of water in the different compartments may be determined from published literature and input into the system or method. This allows us to determine the impact of both the variable fraction of extra-cellular fluid and iron content in the liver on the measured T1 relaxation time.

The simulated measurements of relaxation time for various proportions or fractions of extracellular fluid and hepatic iron content can then be stored for look up 170 and comparison to actual relaxation time measurements obtained. For example, the measured T1 140 can be combined with the measured hepatic iron content 160 to find the extracellular fluid fraction used in the simulation which produces that measured T1 in the presence of that iron content. This extracellular fluid fraction can be compared to the normal extracellular fluid fraction, for example 25%, to determine the presence of inflammation/fibrosis in the liver. In addition, this value of extracellular fluid can be used, for example using the simulated T1 measurement 150, to determine the T1 that would have been measured if the patient's hepatic iron content had been normal 180, to produce an "iron-corrected T1".

The iron-corrected T1 value for a given region of interest (ROI) can determine the presence or absence of fibrosis, and its severity, even in patients with iron overload, for example by defining T1 ranges corresponding to normal, mild (1-2), moderate (3-4) or severe (5-6) fibrosis on the Ishak scale.

Characterizing the parenchymal liver tissue by its iron and extracellular fluid elements, as per the method in FIG. 3, can lead to a diagnosis.

Figure 4:
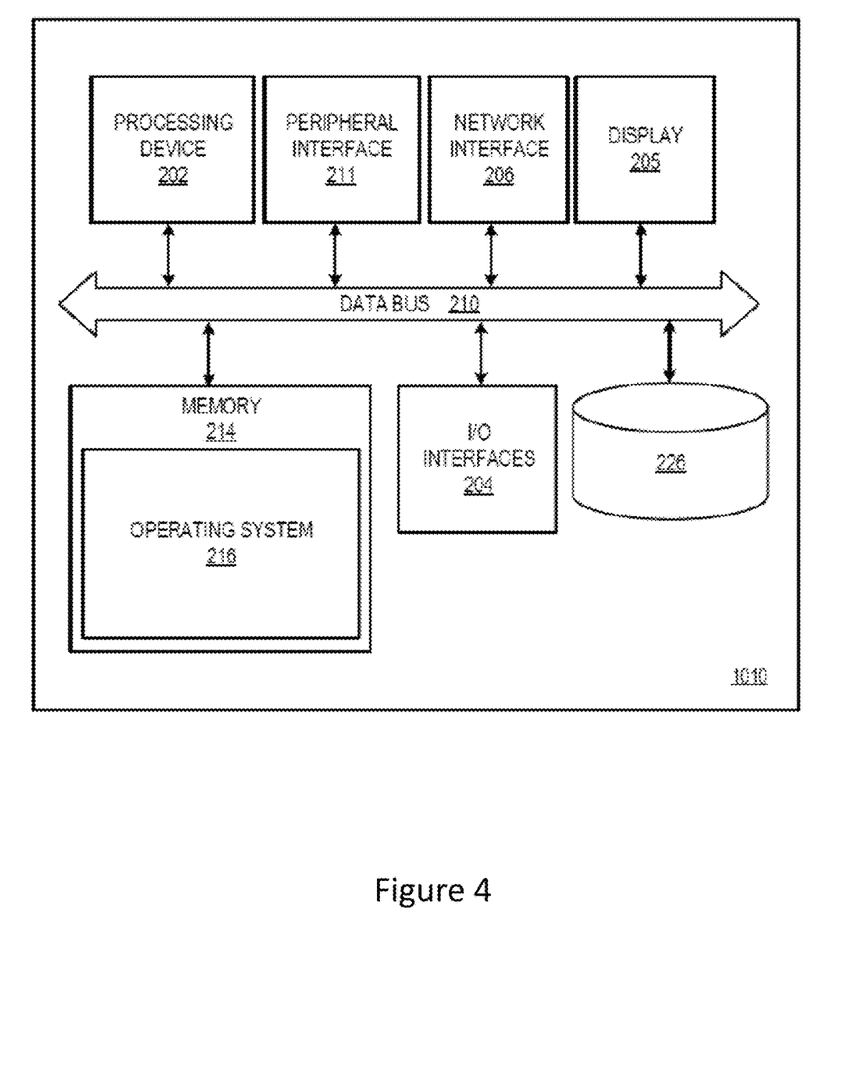
FIG. 4 is a schematic block diagram of an apparatus in which embodiments of the present method for diagnosis of a liver disclosed herein may be implemented.

Reference is now made to FIG. 4, which depicts an apparatus 1010 in which the systems and methods for evaluating liver fibrosis/inflammation in the presence of elevated iron described herein may be implemented. The apparatus 1010 may be embodied in any one of a wide variety of wired and/or wireless computing devices, multi-processor computing device, and so forth. As shown in FIG. 4, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for performing multi-parametric magnetic resonance diagnosis of liver disease described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 4, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over a network 118. The apparatus 1010 may further comprise mass storage 226. The peripheral 211 interface supports various interfaces including, but not limited to IEEE-1394 High Performance Serial Bus, USB, a serial connection, and a parallel connection.

The apparatus 1010 shown in FIG. 4 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate immediate T1 maps available for viewing immediately after image acquisition, thereby allowing re-acquisition on-the-spot if necessary. Examples of apparatus in which the T1 mapping sequences, such as the MOLLI and Sh-MOLLI sequences, may be implemented are described in U.S. Pat. Nos. 5,993,398 and 6,245,027 and U.S. Patent Application Publication No. 2011/0181285, which are incorporated by reference as if fully set forth herein.

The flowchart of FIG. 3 shows examples of functionality that may be implemented in the apparatus 1010 of FIG. 4. If embodied in software, each block shown in FIG. 3 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 4) in a computer system or other system. The machine code may be converted from the source code, etc. If embodied in hardware, each block may represent a circuit or a number of interconnected circuits to implement the specified logical function(s).

Although the flowchart of FIG. 3 shows a specific order of execution, it is understood that the order of execution may differ from that which is depicted. For example, the order of execution of two or more blocks may be scrambled relative to the order shown. Also, two or more blocks shown in succession in FIG. 3 may be executed concurrently or with partial concurrence. Further, in some embodiments, one or more of the blocks shown in FIG. 3 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

Methods and Examples

We investigated the effect of applying our present system and method in-vivo with the resulting MRI measurements of disease being correlated with results of biopsy in homogeneous liver disease. In this example, T1 measurements used the Sh-MOLLI (Piechnik et al., Shortened Modified Look-Locker Inversion recovery (Sh-MOLLI) for clinical myocardial T1-mapping at 1.5 and 3 T within a 9 heartbeat breathhold. J Cardiovasc Magn Reson. 2010 12:69) T1-mapping method at 3 T, on a Siemens Trio, but the invention is equally applicable to other T1-mapping techniques, for example other inversion recovery, saturation recovery or variable flip angle methods. It is also applicable to other field strengths and scanner makes and models.

We split the liver into two components, liver parenchyma (hepatocytes with varying levels of iron) and extracellular fluid (serum albumin), assumed to be mixed on a sub-voxel level. This is shown schematically in FIG. 2. Relaxation times were based on literature values as follows.

Liver Parenchyma

At 1.5 T, transverse relaxivities (in $s^{-1}$) of liver tissue as a function of hepatic iron content (HIC, measured in mg Fe/g dry weight) are given by St Pierre et al., Noninvasive measurement and imaging of liver iron concentrations using proton magnetic resonance. Blood. 2005; 105:855-61 and Wood et al., MRI R2 and R2* mapping accurately estimates hepatic iron concentration in transfusion-dependent thalassemia and sickle cell disease patients. Blood. 2005; 106:1460-5:

$$R2(1.5T)=6.88+26.06\times(HIC)^{0.701}-0.438\times(HIC)^{1.402},$$

$$R2^*(1.5T)=(HIC-0.202)/0.0254.$$

To convert these to relaxivities of liver at 3 T (Ghugre et al. Multi-field behavior of Relaxivity in an Iron-rich environment. Proc Inti Soc Mag Reson Med. 2008; 16:644):

$$R2(3T)=R2(1.5T)\times1.47-2.2$$

$$R2^*(3T)=2\times R2(1.5T)-35.$$

The dependence of longitudinal relaxivity of liver tissue on HIC at 1.5 T is given by Ghugre et al., Mechanisms of tissue-iron relaxivity: nuclear magnetic resonance studies of human liver biopsy specimens. Magn Reson Med. 2005; 54:1185-93, as:

$$R1=R1_0+0.029\times HIC_{wet\_weight}=R1_0+0.029\times 4.1\times HIC,$$

where the scaling factor between dry weight and wet weight HIC is given in Ghugre et al., Mechanisms of tissue-iron relaxivity: nuclear magnetic resonance studies of human liver biopsy specimens. Magn Reson Med. 2005; 54:1185-93. $R1_0$ was the only free parameter in the model, and was set at 0.636/s, such that for normal ECF fraction (25%) and normal HIC (1.2 mg/g) the modeled measured T1 was 819 ms, close to the normal value for hepatic T1 at 3 T (as measured on 50 healthy volunteers using the same Sh-MOLLI protocol). The dependence of R1 on iron concentration was assumed to be the same at 1.5 and 3 T. This was based on the low field-sensitivity of ferritin R1 (Vymazal et al., T1 and T2 of ferritin at different field strengths: Effect on MRI. Magn Reson Med. 1992; 27:367-74), reported limited effect of haemosiderin on T1 (Versluis et al., Detection of cerebral microbleeds: Physical principles, technical aspects and new developments. In: Cerebral Microbleeds ed. Werring O J. Cambridge University Press, 2011; pp 13-21) and low field-dependence of T1 measurements in brain iron-overload (Vymazal et al., The relation between brain iron and NMR relaxation times: An in vitro study. Magn Reson2 Med. 1996; 35:56-61)(caused by a mixture of ferritin and haemosiderin).

Extracellular Fluid

The R1 for plasma at 3 T of 0.44/s was used. See, Rohrer et al., Comparison of magnetic properties of MRI contrast media solutions at different magnetic field strengths. Invest Radiol. 2005; 40:715-24.

Figure 5:
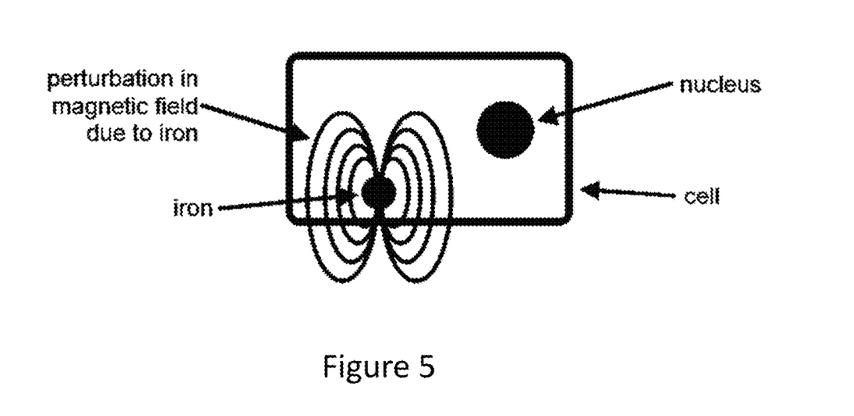
FIG. 5 is a schematic representation of a hepatocyte, demonstrating the extension of the field inhomogeneity outside the cell and into the surrounding material.

The same transverse relaxation times were used for extracellular fluid (ECF) as for liver parenchyma. Water molecules in the cellular environment traverse a distance of several tens of microns even over a typical T2. Koenig et al., Relaxometry of tissue. NMR Encycl. 1996; 6:4108-20. For a normal hepatic iron concentration of 1.2 $mg/g^2$ iron is typically distributed on length scales of 2 μm. Ghugre et al., Relaxivity-iron calibration in hepatic iron overload: Probing underlying biophysical mechanisms using a Monte Carlo model. Magn Reson Med. 2011; 65:837-47. Thus the water in ECF will tend to sample the non-local field inhomogeneities due to iron accumulations (FIG. 5) and the T2 and T2* of these protons will be correspondingly reduced.

Simulations

Figure 6:
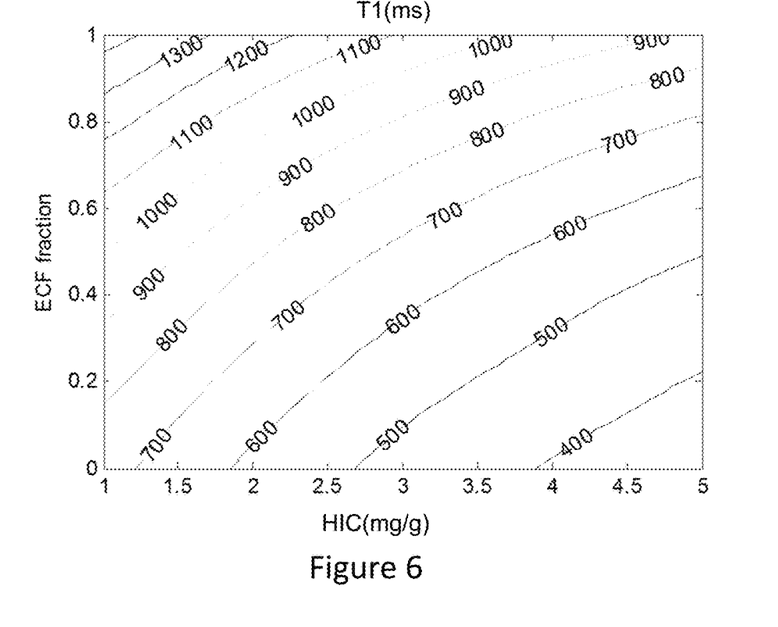
FIG. 6 depicts predicted measured T1 values in milliseconds produced by a ShMOLLI fit from Bloch simulations of an exemplary two-compartment liver model.

The relaxation times from above were used in full Bloch simulations of the Sh-MOLLI (Piechnik et al., Shortened Modified Look-Locker Inversion recovery (Sh-MOLLI) for clinical myocardial T1-mapping at 1.5 and 3 T within a 9 heartbeat breathhold. J Cardiovasc Magn Reson. 2010 12:69) sequence, implemented in Matlab. This sequence is used as an example, but the method can be generally applied to any T1-mapping sequence. The two components were simulated separately, for hepatic iron concentrations ranging from 1-5 mg/g. The complex signal amplitudes were combined with the fraction of ECF ranging from 0 to 100%. The magnitude and phase were calculated and then fitted using the Sh-MOLLI reconstruction algorithm (Piechnik et al., Shortened Modified Look-Locker Inversion recovery (Sh-MOLLI) for clinical myocardial T1-mapping at 1.5 and 3 T within a 9 heartbeat breathhold. J Cardiovasc Magn Reson. 2010 12:69), implemented in IDL. This produced a predicted measured T1 value for each combination of iron and ECF concentrations. There was some variation in the validation data in the precise acquisition parameters (particularly the number of phase encode lines) used, so parameters from a number of patient scans were simulated and then an average taken to produce the data shown in FIG. 6.

MRI Data Acquisition

Using a Siemens Verio 3 T MR scanner, T1 maps were acquired using an EGG gated Sh-MOLLI sequence on a transverse slice through the liver, using the following acquisition parameters: TR 2.14 ms, TE 1.07 ms, flip angle 35°, matrix size 192×144 †, field-of-view 360 mm×270 mm†, slice thickness 6 mm and a GRAPPA acceleration factor of 2. The dagger (†) denotes variable acquisition parameters. T2* maps for the same slice were calculated from an ECG-gated multi-echo RF-spoiled gradient-echo sequence the following parameters: TR 26.5 ms, TE=2.46, 7.38, 12.30, 17.22 and 22.14 ms (water and fat in phase), flip angle 20°, matrix size 192×144 †, field-of-view 360 mm×270 mm†, slice thickness 3 mm, and a GRAPPA acceleration factor of 2. Again, the dagger (†) denotes variable acquisition parameters. The T2* maps were calculated using a linear fit to the log-transformed reconstructed pixel values.

Correcting T1

Two regions of interest (ROIs), matched as closely as possible on the two maps and avoiding large vessels, were drawn on the T1 and T2* map for each patient. One ROI was placed laterally (aiming to match the approximate location of transcutaneous liver biopsy) and one medially. The mean T1 and T2* over each ROI was calculated. For this analysis, the two measurements of each relaxation time were averaged before being used to correct the T1.

The matrix of predicted measured T1 was used as a look-up table, as follows. For each patient the hepatic iron content was calculated using the relation (Wood et al., MRI R2 and R2* mapping accurately estimates hepatic iron concentration in transfusion-dependent thalassemia and sickle cell disease patients. Blood. 2005; 106:1460-5 and Ghugre et al., Multi-field behavior of Relaxivity in an Iron-rich environment. Proc Inti Soc Mag Reson Med. 2008; 16:644):

$$HIC=(0.202+0.0254*(R2*+35)/2).$$

The measured T1 was then compared to the predicted measured T1 for that measured iron content. This T1 was associated with a particular ECF fraction, which could be used as a proxy for fibrosis or used to calculate the T1 which we predict would be measured if the patient had normal liver iron (1.2 mg/g), known as the "corrected T1". The process is shown schematically in FIG. 3.

Validation

The resulting iron corrected T1 was compared to the Ishak scores for fibrosis ascertained from biopsy. Liver biopsies were assessed by the pathology team and graded by consensus from 0 (normal) to 6 (cirrhosis) on the Ishak score for fibrosis. Ishak et al., Histological grading and staging of chronic hepatitis. J Hepatol. 1995; 22:696-9. In this model, ECF was used as a biomarker for fibrosis, although this could be confounded by inflammation. Agreement between Ishak score and T1 was tested using Spearman's rank correlation coefficient.

There are two possible confounding factors when comparing between T1 measurements and Ishak scores from biopsy, as follows:

Patchy disease (defined here as the mean T1 in the two ROIs having a difference greater than 50 ms) gives rise to two sub-problems:
  Firstly, the biopsy location in the liver is unknown, so it is unclear whether a more or less diseased portion of the liver has been assessed by biopsy.
  Secondly, ROI-based iron correction may under/overestimate effect of iron if ROIs are not well matched. Averaging over the two ROIs will also exacerbate this effect as the effect of iron on measured T1 is non-linear.

Pericellular fibrosis (PF). The Ishak scoring system was developed for the staging of fibrosis in patients with viral hepatitis, in which fibrosis spreads through the liver in a characteristic way, with thickening of the connective tissue around the portal tracts, which then gradually begins to bridge between portal tracts. In, for example, fatty liver disease, it is relatively common to see pericellular fibrosis (rather than periportal fibrosis), so there may be a relatively large volume of fibrosis, but which receives a low score on the Ishak scale. When pericellular fibrosis has been noted on the pathology report, this was included as a flag in the data for analysis.

In order to assess the performance of the model-based iron correction algorithm on as "pure" a set of data as possible, patients were excluded from the validation if they had either MR-defined patchy disease (where the part of the liver sampled by the biopsy is unknown, and the iron correction may not work well) or biopsy-reported pericellular fibrosis (where the Ishak score is known to underestimate the extent of fibrotic disease).

Results and Discussion

Shown in Table 1 are Spearman rank correlation coefficients (R) for the correlation between T1 (both before and after correction) and Ishak score. Data are presented separately for patients with normal and abnormal iron, to demonstrate the impact of iron on the T1 measurement and the effectiveness of the correction algorithm. The number of patients is shown in brackets and statistically significant correlations at the p<0.05 level are starred.

Figure 1:
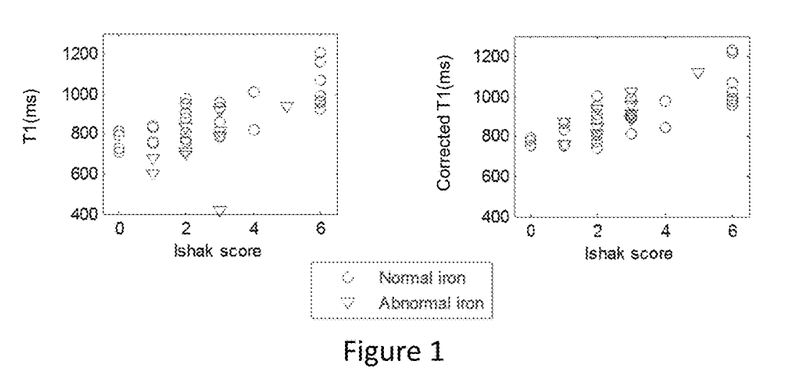

FIG. 1 demonstrates graphically the effect of the iron correction, in particular the qualitatively large improvement in correlation after T1 correction.

The data for uncorrected T1 demonstrate that iron is clearly a problem for correlation between Ishak score and T1.

Applying the iron correction has two main effects: firstly, the correlation between corrected T1 and Ishak score is statistically significant for patients with abnormal iron; secondly, the correlation coefficient for patients with abnormal iron is increased so that it is similar to that for patients with normal iron.

TABLE 1

|  | Uncorrected T1 | Corrected T1 |
|---|---|---|
| Normal Fe (n = 29) | 0.77* | 0.77* |
| Abnormal Fe (n = 10) | 0.58 | 0.80* |

The correction of T1 for iron using a model-based approach was thus shown to improve the rank correlation between T1 and Ishak score, a biopsy measure of liver fibrosis. This demonstrates that this model of the magnetic resonance behaviour of the liver in the presence of varying iron and extracellular fluid enables correction of T1 for the confounding effects of high iron, and thus a more precise non-invasive quantification of fibrosis than methods using T1 measurements alone.

It should be emphasized that the above-described embodiments are merely examples of possible implementations. It is possible to include exchange of protons between the two compartments based on the known exchange rate of water in hepatocytes (Bacic et al. NMR study of water exchange across the hepatocyte membrane. Magn Reson Imaging 1989; 7:411-416). Similarly, a third compartment (the so-called "bound pool" consisting of water protons closely bound to proteins and with very short T2) can be included, and the magnetisation transfer effects on the T1 measurement included in the simulation (Graham and Henkelman. Understanding pulsed magnetisation transfer. J Magn Reson Imaging 1997; 7:903-912). Instead of fixed T2 and T1 as a function of iron content, the compartment relaxation times can also vary as a function of ECF fraction. As the ECF fraction increases, if one assumes a constant number of Kupffer cells in the sinusoids but an increasing volume of fluid periportally, the mean T1 and T2 of this compartment increase. This effect could also be modelled by splitting the ECF compartment into sinusoidal and periportal/portal/vascular regions. Finally, it is possible to model the transverse relaxation times in the various compartments using Monte Carlo modelling (Ghugre and Wood. Relaxivity-iron calibration in hepatic iron overload: probing underlying biophysical mechanisms using a Monte Carlo model. Magn Reson Med 2011; 65:837-847).

These methods could also be applied to other organs, particularly when Monte Carlo methods (Ghugre and Wood. Relaxivity-iron calibration in hepatic iron overload: probing underlying biophysical mechanisms using a Monte Carlo model. Magn Reson Med 2011; 65:837-847) are used to establish the relationship between T2 and iron content in tissues where biopsy is not routine or possible, for example the spleen and heart, based on either known or assumed iron distributions within the tissue of interest.

A similar process could be used for other T1-mapping methods and different MR field strengths, for example, 1.5 Tesla. Many variations and modifications may be made to the above-described embodiments without departing from the principles of the present disclosure. All such modifications and variations are intended to be included herein within the scope of this disclosure and protected by the following claims.

The invention claimed is:

1. A computer-implemented method for processing MR relaxometry data of visceral tissue of a subject, comprising:
   a) positioning a subject in relation to a magnetic resonance (MR) scanner;
   b) selecting a region of interest of the subject having one or more visceral organs of interest for relaxometry data acquisition;
   c) obtaining, by the scanner, measurements of measured relaxometry data of a subject's visceral tissue for extracellular fluid from the region of interest of the subject using a relaxometry data acquisition method, the relaxometry data acquisition method having relaxometry data acquisition parameters;
   d) determining a measured iron content for the visceral tissue of the region of interest of the subject using an iron content determination method;
   e) (1) simulating, by a computing device, measurements of simulated relaxometry data for various proportions or fractions of extracellular fluid and iron content in the visceral tissue using relaxometry data acquisition parameters from step (c) to produce predicted extracellular fluid values based on various proportions or fractions of extracellular fluid and iron content in the visceral tissue and determining from said simulation a predicted extracellular fluid fraction value which produces the measured relaxometry data in the presence of the measured iron content; or
      (2) comparing, by the computing device, the measured relaxometry data and measured iron content to a look-up table which contains measurements of simulated relaxometry data for various proportions or fractions of extracellular fluid and iron content in the visceral tissue, and determining from said comparison a predicted extracellular fluid fraction value which produces the measured relaxometry data in the presence of the measured iron content;
   f) comparing, by the computing device, the predicted extracellular fluid fraction value to the measurements of simulated relaxometry data obtained in Step (e), part (1), or to the look-up table of Step (e), part (2), to determine an iron-corrected value of relaxometry data of the subject's visceral tissue based on the predicted excellular fluid fraction value and a normal iron content for the visceral tissue; and
   g) outputting the iron-corrected relaxometry data to a display.

2. The method of claim 1, wherein the relaxometry data includes one or more characteristic relaxation time or times in tissue in the visceral tissue.

3. The method of claim 1, wherein the relaxometry data acquisition method is T1 mapping and the iron content determination method includes one or more of T2 mapping, T2* mapping, magnetic resonance spectroscopy, or measuring one or more blood biomarkers.

4. The method of claim 3, wherein the T1 mapping is performed using a modified Look Locker inversion (MOLLI) recovery pulse sequence or a shortened modified Look Locker inversion recovery (Sh-MOLLI) sequence.

5. The method of claim 1, wherein the simulation includes the impact of measured iron content in the visceral tissue on both the intra- and extracellular relaxation times in multi-compartment modeling of various fractions of extracellular fluid in the visceral tissue.

6. The method of claim 1, wherein the simulation includes the impact of measured iron content on both the intra- and extracellular fluid relaxation times and simulating a predicted measurement of the visceral tissue for various fractions of extracellular fluid in combination with a simulation of an imaging sequence.

7. The method of claim 1, wherein the simulation involves a Bloch equation simulation, with or without exchange between intra- and extra-cellular fluid compartments, and with or without magnetisation transfer effects.

8. The method of claim 1, wherein the visceral tissue is liver, spleen or heart.

9. A non-transitory computer redable medium comprising instructions for configuring a processor to carry out the steps of the method of claim 1.

10. The method of claim 1, wherein the visceral tissue is liver.

11. The method of claim 1, further comprising:
   i) determining, by the computing device, an Ishak scale value from the iron-corrected relaxometry data; and
   j) outputting the Ishak scale value to a display.

12. The method of claim 1, further comprising:
   i) comparing, by the computing device, the predicted extracellular fluid fraction value and the normal extracellular fluid fraction to determine disease status; and
   j) outputting the disease status.

13. The method of claim 1, wherein the simulation of step (e) further comprises generating a look up table containing predicted extracellular fluid values based on various proportions or fractions of extracellular fluid and iron content in the visceral tissue.

14. A system, comprising:
   at least one computing device;
   at least one application executable in the at least one computing device, the at least one application comprising logic that:
   a) obtains measurements of measured relaxometry data of a subject's visceral tissue for extracellular fluid;
   b) determines a measured iron content for the visceral tissue;
   c) simulates measurements of relaxometry data of the subject's visceral tissue for extracellular fluid for the determined iron content;
   d) compares the measurement of the subject's visceral tissue for extracellular fluid of step (a) to the simulated measurements of the subject's visceral tissue for extracellular fluid of step (c) and to simulated measurements of relaxometry data for various proportions or fractions of extracellular fluid and iron content in the visceral tissue, and determining from said comparison the extracellular fluid fraction value used in the simulation which produces the measured relaxometry data in the presence of that iron content; and e) determines from the simulated measurements of relaxometry data for various proportions or fractions of extracellular fluid and iron content in the visceral tissue of step (d) a value of relaxometry data of the subject's visceral tissue for the extracellular fluid fraction value determined in step (d) based on a normal iron content for the visceral tissue.

15. The system of claim 14, wherein the logic further determines from said measurements and comparison the presence or absence of visceral tissue fibrosis or inflammation.

16. The system of claim 14, wherein the relaxometry data is obtained by use of a medical imaging device including a magnetic resonance (MR) scanner and the device is used to measure one or more characteristic relaxation time or times in the visceral tissue.

17. The system of claim 14, wherein the visceral tissue is measured for extracellular fluid using T1 mapping and the visceral tissue is measured for iron content using one or more of one or more of T2 mapping, T2* mapping, magnetic resonance spectroscopy, or measuring one or more blood biomarkers.

18. The system of claim 17, wherein the T1 mapping is performed using a modified Look Locker inversion (MOLLI) recovery pulse sequence or a shortened modified Look Locker inversion recovery (Sh-MOLLI) sequence.

19. The system of claim 14, wherein the simulation includes the impact of iron content in the visceral tissue on both the intra- and extracellular relaxation times in multi-compartment modeling of various fractions of extracellular fluid in the visceral tissue.

20. The system of claim 14, wherein the simulation includes the impact of iron content on both the intra- and extracellular fluid relaxation times and simulating a predicted measurement of the visceral tissue for various fractions of extracellular fluid in combination with a simulation of an imaging sequence.

21. The system of claim 14, wherein the visceral tissue is liver, spleen or heart.

22. The system of claim 14, wherein the visceral tissue is liver.

23. The system of claim 14, further comprising logic that:
i) determines an Ishak scale value from the iron-corrected relaxometry data; and
j) outputs the Ishak scale value to a display.

24. The system of claim 14, further comprising logic that:
i) compares the predicted extracellular fluid fraction value and the normal extracellular fluid fraction to determine disease status; and
j) outputs the disease status.

* * * * *